US006660489B2

(12) United States Patent
Schrecengost et al.

(10) Patent No.: US 6,660,489 B2
(45) Date of Patent: Dec. 9, 2003

(54) ATP EXTRACTION METHOD

(75) Inventors: Leanne M. Schrecengost, Abingdon, MD (US); Jon C. Wannlund, Parkton, MD (US); Robert W. Rosenstein, Ellicott City, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/933,985

(22) Filed: Aug. 21, 2001

(65) Prior Publication Data

US 2002/0068309 A1 Jun. 6, 2002

Related U.S. Application Data

(60) Provisional application No. 60/250,118, filed on Dec. 1, 2000.

(51) Int. Cl.$^7$ ................................................ C12Q 1/66
(52) U.S. Cl. ............................ 435/8; 435/31; 435/259
(58) Field of Search ........................... 435/4, 8, 29, 31, 435/259; 436/18

(56) References Cited

U.S. PATENT DOCUMENTS

| 4,014,745 | A | * | 3/1977 | Fletcher et al. | ................. | 435/8 |
|---|---|---|---|---|---|---|
| 4,303,752 | A | | 12/1981 | Kolehmainen et al. | ......... | 435/8 |
| 5,004,684 | A | * | 4/1991 | Simpson et al. | ................. | 435/8 |
| 5,558,986 | A | * | 9/1996 | Lundin | ........................... | 435/4 |
| 5,618,682 | A | | 4/1997 | Scheirer | ........................ | 435/8 |
| 5,641,641 | A | | 6/1997 | Wood | ............................. | 435/8 |
| 5,895,751 | A | * | 4/1999 | Hattori et al. | .................. | 435/8 |
| 5,908,751 | A | * | 6/1999 | Higo et al. | ..................... | 435/6 |
| 6,238,857 | B1 | * | 5/2001 | Hattori et al. | .................. | 435/4 |

FOREIGN PATENT DOCUMENTS

| EP | 0 299 601 B1 | 1/1989 | ............ C12Q/1/66 |
|---|---|---|---|
| WO | WO 00/49171 | 8/2000 | ............ C12Q/1/04 |

* cited by examiner

*Primary Examiner*—Ralph Gitomer
(74) *Attorney, Agent, or Firm*—Bruce S. Weintraub

(57) ABSTRACT

A method for extracting ATP from a biological sample is disclosed. The method involves introducing a cationic extractant and an anionic substance and then extracting ATP. The method may be used to assay for the presence of ATP in a biological sample or to determine the amount of ATP extracted from a biological sample. The method is particularly useful in detecting contamination on surfaces and in food products. A reagent, a test device and a test kit that involve the use of the method to detect contamination are also disclosed.

15 Claims, 10 Drawing Sheets

ATP EXTRACTION METHOD

This application claims priority from U.S. Provisional Application Ser. No. 60/250,118, which was filed Dec. 1, 2000. The entirety of that provisional application is incorporated herein by reference.

BACKGROUND OF THE INVENTION

1. Field of the Invention

The present invention relates to a method for the extraction of ATP from a microorganism and, more particularly, to a method for such an extraction that reduces subsequent distortions on assay with luciferase. The method of the invention is particularly useful in the ATP-luciferin-luciferase assay, which is commonly used to monitor microorganism contamination in the food manufacturing industry.

2. Background of the Technology

Many industries have a need for rapid microbial or "bioburden" monitoring. One of the most visible industries with this requirement is the food manufacturing industry. Food manufacturers are typically required, through governmental regulation or through internal operating procedures, to monitor (1) incoming raw materials, (2) in-process manufacturing areas, (3) manufacturing surfaces and/or (4) the food items themselves for contamination with microorganisms. In general, these manufacturers are interested in measuring only viable or living organisms as opposed to non-viable organisms, which do not present a threat to human health.

One method that has gained importance for these applications involves the use of adenosine triphosphate ("ATP") bioluminescence ("ATP bioluminescence"), wherein the firefly luciferin/luciferase system and ATP extracted from a microbial sample are used. If present in a sample, ATP, which is an energy molecule found in all living cells, combines with luciferin in the presence of magnesium ion at approximately neutral pH to form an ATP magnesium-luciferin complex. This combination seems to be driven by charged interactions. The ATP-magnesium-luciferin complex then interacts with the enzyme luciferase in the presence of oxygen to produce light, the intensity of which can be detected using a sensitive light detector. The intensity, measured in relative light units ("RLUs"), is directly proportional to the amount of ATP in the sample, and thus can be correlated with the level of microorganisms in the sample. It is well known in the art that only viable or live organisms have measurable levels of ATP. In the case of non-viable organisms, the ATP originally present would have been converted to ADP or AMP by normal biological processes and would be, therefore, unavailable for measurement in the firefly luciferin-luciferase system.

There are several drawbacks associated with prior known ATP-luciferin-luciferase assay methods, including:

1. The enzyme luciferase is labile and, therefore, has a relatively short period of activity in the purified state. Once deterioration of this enzyme occurs, light output (intensity) decreases;
2. The extraction procedures commonly used to liberate ATP from microorganisms in a sample usually involve the use of cationic extractants such as benzalkonium chloride, benzethonium chloride and dodecyl trimethyl ammonium bromide. Cationic extractants are known to have a negative affect on luciferase, presumably by interacting with its active site. Use of cationic extractants, therefore, negatively affects the output of light generally observed during ATP-luciferin-luciferase interaction. See Siro et al., European Journal of Applied Microbiology and Biotechnology; 15:258–64 (1982) and Lundin, Analytical Applications of Bioluminescence and Chemiluminescence, Kricka et al., (eds.), Academic Press, London (1984); and
3. The substances commonly used as sanitizers in sample collection and preparation usually contain harsh substances, eg., bleach, sodium tri-phosphate and quaternary ammonium salts. These substances are also known to have a negative affect on luciferase activity. Similar to the use of cationic extractants, use of such substances during sample collection affects the output of light generally observed during ATP-luciferin-luciferase interaction.

U.S. Pat. No. 5,188,965 discloses a means to remedy drawback (1) above, wherein luciferase is presented in a test device in a dried and, therefore, more stabilized state.

One attempt to remedy drawback (2) above, has been to dilute the cationic extractant prior to use. For example, extraction methods such as that described in the 1980's literature, which involve the use of, e.g., trichloroacetic acid or dimethyl sulfoxide (DMSO), although effective in extracting ATP from samples, required dilution of the ATP extract prior to light measurement. See Stanley, Methods in Enzymology, 133:14–22 (1986). Unfortunately, this methodology adds steps and time to the overall process and diminishes assay sensitivity.

Attempts to remedy drawback (3) above involve removal of the harsh substance(s) prior to assay. Such attempts, which add steps and time to the overall process, also diminish assay sensitivity.

U.S. Pat. No. 5,004,684 discloses another attempt to alleviate the negative effects of commonly used extractants, as well as to simplify the testing process (i.e., by reducing the number of required steps). According to U.S. Pat. No. 5,004,684, neutral or non-ionic detergents, e.g., polyoxyethylene sorbitan monooleate (Tween 80) and the like, are added to the extraction reaction mixture. The neutral or non-ionic detergents apparently prevent interaction between the cationic detergent and the hydrophobic active site of luciferase (see DeLuca, Purification and Properties of Firefly Luciferase, Methods in Enzymology, 57:3–15; Denburg et al., Arch. Biochem. Biophys., 141:668 (1970)). Although the method disclosed in U.S. Pat. No. 5,004,684 has proven effective, there remains a need in the industry for improved assay sensitivity.

SUMMARY OF THE INVENTION

It is an object of the invention to provide a method for extracting ATP from a biological sample.

Another object of the invention is to provide a method for assaying for the presence of ATP in a biological sample.

Yet another object of the invention is to provide a method for detecting the amount of ATP extracted from a biological sample.

A further object of the invention is to provide a method for detecting contamination. The method can be used, for example, for detecting contamination on a surface or in a food product.

Yet a further object of the invention is to provide a reagent, a test device and a test kit for detecting contamination of a sample.

In accordance with the above objects, the method for ATP extraction involves introducing a cationic extractant and anionic substance to extract the ATP. The anionic substance neutralizes a positive charge of the cationic extractant.

The anionic substance is preferably a sulfate ion, more preferably in the form of a magnesium salt, or SDS. The magnesium salt is preferably present in an amount of about 0.0001 µg to about 0.4 µg, and the SDS is preferably present in an amount of about 0.0001 µg to about 0.5 µg.

The method for assaying for the presence of ATP in a biological sample involves introducing a cationic extractant and anionic substance to extract ATP from the biological sample; permitting luciferin and magnesium to react with the extracted ATP to form an ATP-magnesium-luciferin complex; allowing the ATP-magnesium-luciferin complex to interact with luciferase, wherein light is produced; and measuring the intensity of the light, wherein the presence of light corresponds to the presence of ATP.

The method for detecting the amount of ATP extracted from a microorganism involves introducing a cationic extractant and anionic substance to extract the ATP; permitting luciferin and magnesium to react with the extracted ATP to form an ATP-magnesium-luciferin complex; allowing the ATP-magnesium-luciferin complex to interact with luciferase, wherein light is produced; measuring the intensity of the light, wherein the intensity of the light corresponds to the amount of ATP extracted.

The method for detecting contamination in a sample involves extracting ATP from the sample by introducing a cationic extractant and anionic substance to extract the ATP from any microorganisms present therein; permitting luciferin and magnesium to react with the extracted ATP to form an ATP-magnesium-luciferin complex; allowing the ATP-magnesium-luciferin complex to interact with luciferase, wherein light is produced; and measuring the intensity of the light, wherein the intensity of the light corresponds to an amount of ATP extracted, and wherein the amount of ATP extracted corresponds to contamination.

The methods described above may be conducted in the presence of sanitizers commonly used in biological sample collection and preparation.

The test device for performing the above-described method includes a reagent source having the reagents required for the bioluminescence assay contained therein in solid form.

The reagents include a reagent comprising a cationic extractant and an anionic substance. The reagents may further include all substances necessary to carry out the bioluminescence assay, including at least one bioluminescence reagent.

The test kit includes a reagent containing at least a cationic extractant and an anionic substance and, optionally, a bioluminescence reagent. The test kit may include the reagent(s) in the form of a test device.

DETAILED DESCRIPTION OF THE INVENTION

Figure 1:
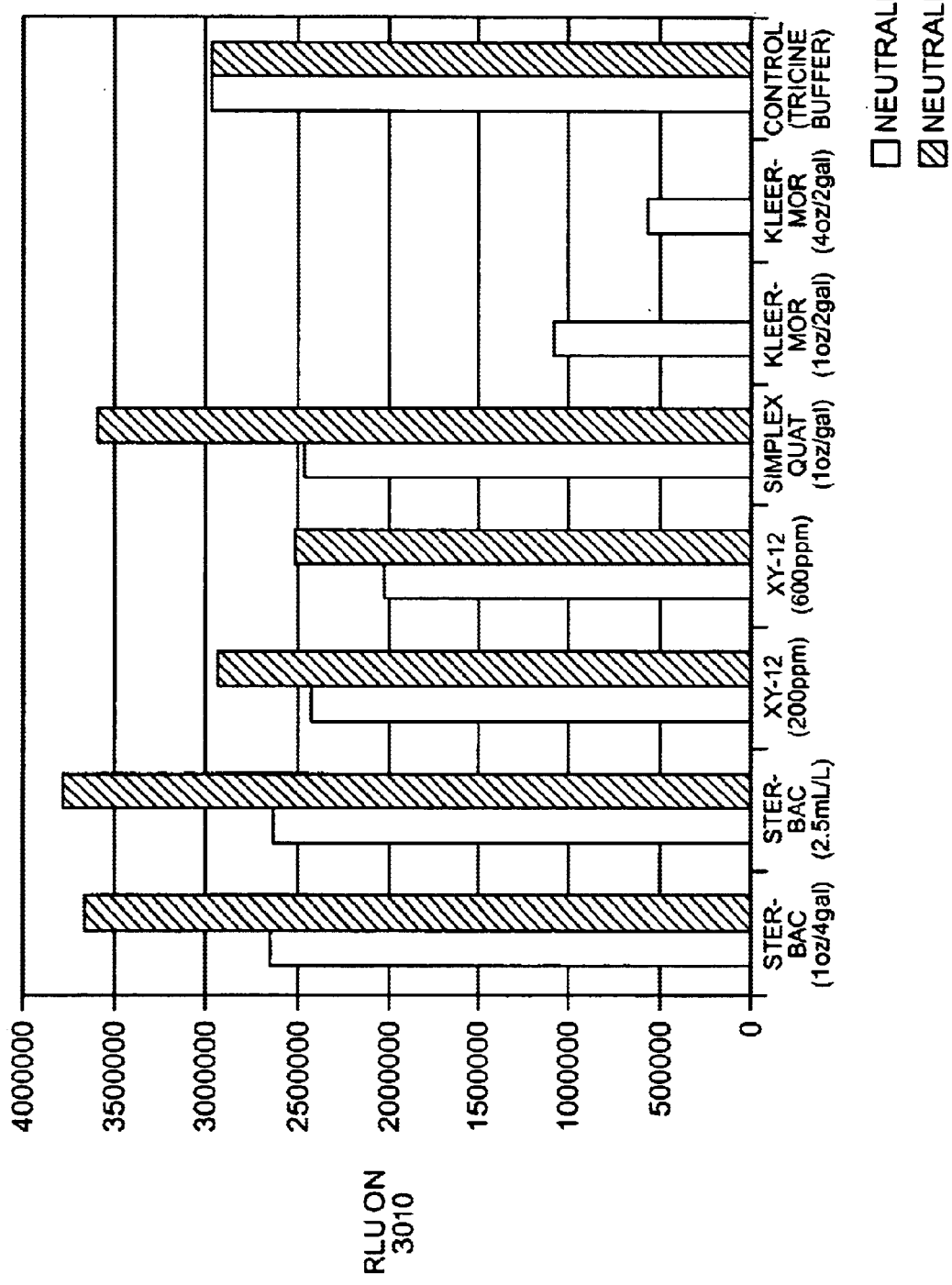
FIG. 1 shows a comparison of the effect of Tween® 20 and $MgSO_4$ on the intensity of light in the presence of various sanitizers and ATP-luciferin-luciferase solution.

The present inventors have surprisingly discovered that negatively charged (i.e., anionic) substances, and in particular sulfate ion or sodium dodecyl sulfate ("SDS"), at appropriate concentrations, effectively neutralize the negative effects of positively charged extractants commonly used to remove ATP from a biological sample. The present inventors have also discovered that these negatively charged substances are particularly effective in the firefly luciferin/luciferase system. The inventors have further discovered that these negatively charged substances are capable of functioning in the presence of sanitizers commonly used in biological sample collection and preparation.

It was unexpected that a small molecule like sulfate ion would function as a neutralizer. It was also unexpected that SDS, at an appropriate concentration, would effectively function as a neutralizer for positively charged extractants. Although SDS, which is generally used as a disrupter of protein structure, has been found to completely eliminate the light reaction if it is present at too high a concentration, SDS, at appropriate concentrations, effectively functions as a neutralizer for positively charged extractants.

The present invention thus involves the use of negatively charged substances, and in particular sulfate ion or SDS, at appropriate concentrations to neutralize the negative effects of ATP extractants.

It is likely that the sulfate ion (or the SDS) functions as a neutralizer by neutralizing the positive charge of the extractant. Once this is done, any interference of the extractant with the binding of the ATP-magnesium-luciferin complex to the luciferase active site is eliminated.

The present invention provides a method for extracting ATP from a biological sample. In accordance with the extraction method of the present invention, a negatively charged substance, particularly sulfate ion or SDS, is employed during ATP extraction to neutralize the positive charge of commonly used extractants. The anionic substance can be used with extractants such as benzalkonium chloride, benzethonium chloride and dodecyl trimethyl ammonium bromide.

The invention also provides a method for assaying for the presence of ATP in a biological sample. In accordance with the assay method of the present invention, a negatively charged substance, particularly sulfate ion or SDS, is employed during ATP extraction to neutralize the positive charge of extractants commonly used to liberate ATP from the sample; luciferin and magnesium are permitted to react with the liberated ATP; an ATP-magnesium-luciferin complex is formed; the ATP-magnesium-luciferin complex interacts with luciferase to produce light; and light intensity, which corresponds directly to the concentration of ATP, is measured. The intensity of light can be measured in, e.g., a luminometer.

The invention also provides a reagent for extracting ATP from a biological sample. The reagent comprises a commonly used ATP extractant and a negatively charged substance, in particular sulfate ion or SDS. The negatively charged substance is capable of neutralizing the positive charge of the ATP extractant.

The reagent can further include all substances necessary to carryout the bioluminescence assay, including a bioluminescence reagent. The bioluminescence reagent preferably contains luciferin and luciferase alone or in combination with magnesium.

The reagent can be provided in liquid or solid form. If provided in solid form the reagent (test device) can be, for example, a sheet of solid carrier material having one or more of the reagents required for the bioluminescence assay contained therein or thereon. The solid carrier material can be of a size and shape such that it fits in an interior surface of a test well through which light output can be measured. The solid carrier material can be, for example, paper.

The invention further provides a method for monitoring contamination on a surface or in a commodity. In accordance with the monitoring method, a negatively charged substance, and in particular sulfate ion or SDS, is employed during ATP extraction to neutralize the positive charge of extractants commonly used to liberate ATP from the surface or the commodity; luciferin and magnesium are permitted to react with the liberated ATP; an ATP-magnesium-luciferin complex is formed; the ATP-magnesium-luciferin complex interacts with luciferase to produce light; and light intensity, which corresponds directly to the concentration of ATP, is measured, wherein an increased light intensity as compared to a control indicates the presence of contamination.

In accordance with a preferred embodiment of the invention, sulfate in the form of a magnesium salt at an appropriate concentration is employed as the negatively charged substance. It was unexpected that sulfate could be added to the reaction mixture as a magnesium salt. Although magnesium is required for the light reaction, it is generally used as a chloride salt due to anticipated sulfate inhibition. By adding the sulfate as a magnesium salt, a single reagent that accomplishes two needs, i.e., the presence of sulfate as a neutralizer during ATP extraction and the presence of magnesium ion, a necessary component for the light reaction, during subsequent assay, is used.

As discussed herein, a disadvantage of prior known ATP-luciferin-luciferase methodologies has been the number of steps in the reaction sequence. In accordance with an embodiment of the invention, sulfate ion, e.g., in the form of magnesium sulfate, can be dried onto a test device, thereby eliminating the step of adding neutralizer prior to the ATP-luciferin-luciferase light generation reaction.

According to another embodiment of the invention, all of the necessary chemical components for the reaction can be incorporated in a dried state into a well or disposable design. This can be done, e.g., in accordance with the procedures disclosed in U.S. Pat. No. 5,188,965, the entire contents of which are incorporated by reference herein. In accordance with this embodiment, the luciferin, the luciferase and optionally the magnesium are bound to carrier material to maintain the reagents in close proximity to a transparent wall through which light is measured. One would then only have to add sample extracted in accordance with the invention to the well or appropriately designed disposable.

The invention will now be described in the following non-limiting examples.

EXAMPLES

ATP-luciferin-luciferase assays were conducted to determine the effect of the following on assay activity: (1) Tween® 20 (2% Tween® 20 in 50 mM tricene buffer, pH 6.75), (2) $MgSO_4$ (0.229 g/L in 50 mM tricene buffer, pH 7.46), (3) SDS (0.268 g/L in 50 mM tricene buffer, pH 7.61) and (4) a combination of $MgSO_4$ and various amounts of Tween®. Each of these substances were assayed alone and in the presence of a commonly used positively charged ATP extractant, i.e., benzalkonium chloride (0.3325 g/L). Many of the assays were conducted in the presence of the following sanitizers: Ster-Bac® (1 oz/4 gal); Ster-Bac® (2.5 ml/L); XY-12 (200 ppm); XY-12 (600 ppm); Simplex Quat (1 oz/gal); Kleer-Mor® (1 oz/2 gal); and Kleer-Mor® (4 oz/2 gal). The $MgSO_4$ and SDS assays were conducted using molar concentrations of $MgSO_4$ and SDS equal to that of the positively charged extractant, as well as using molar concentrations of $MgSO_4$ and SDS diluted as compared to that of the positively charged extractant.

Protocol

Depending on the substance being tested, sanitizer, neutralizer (i.e., Tween® 20, $MgSO_4$ or SDS), ATP solution, luciferin/luciferase cocktail, extractant and/or benzalkonium chloride (in various combinations) were placed in a cuvette and light intensity was read. Each sanitizer was run in duplicate. A control tube containing buffer and ATP was also run. Light output was measured in a Monolight 3010 luminometer. Each experiment was conducted in total volume of 0.42 ml in the curvette.

FIG. 1 compares the effect of Tween® 20 and $MgSO_4$ on the intensity of light in the presence of extractant (benzalkonium chloride (0.3325 g/L ATP-free water)), ATP-luciferin-luciferase solution (tricene buffer) and various sterilizers, i.e., (1) Ster-Bac® (1 oz/4 gal), (2) Ster-Bac® (2.5 ml/L), (3) XY-12 (200 ppm), (4) XY-12 (600 ppm), (5) Simplex Quat (1 oz/gal), (6) Kleer-Mor® (1 oz/2 gal) and (7) Kleer-Mor® (4 oz/2 gal); and in the presence of (8) a Control (tricene buffer only)).

Figure 2:
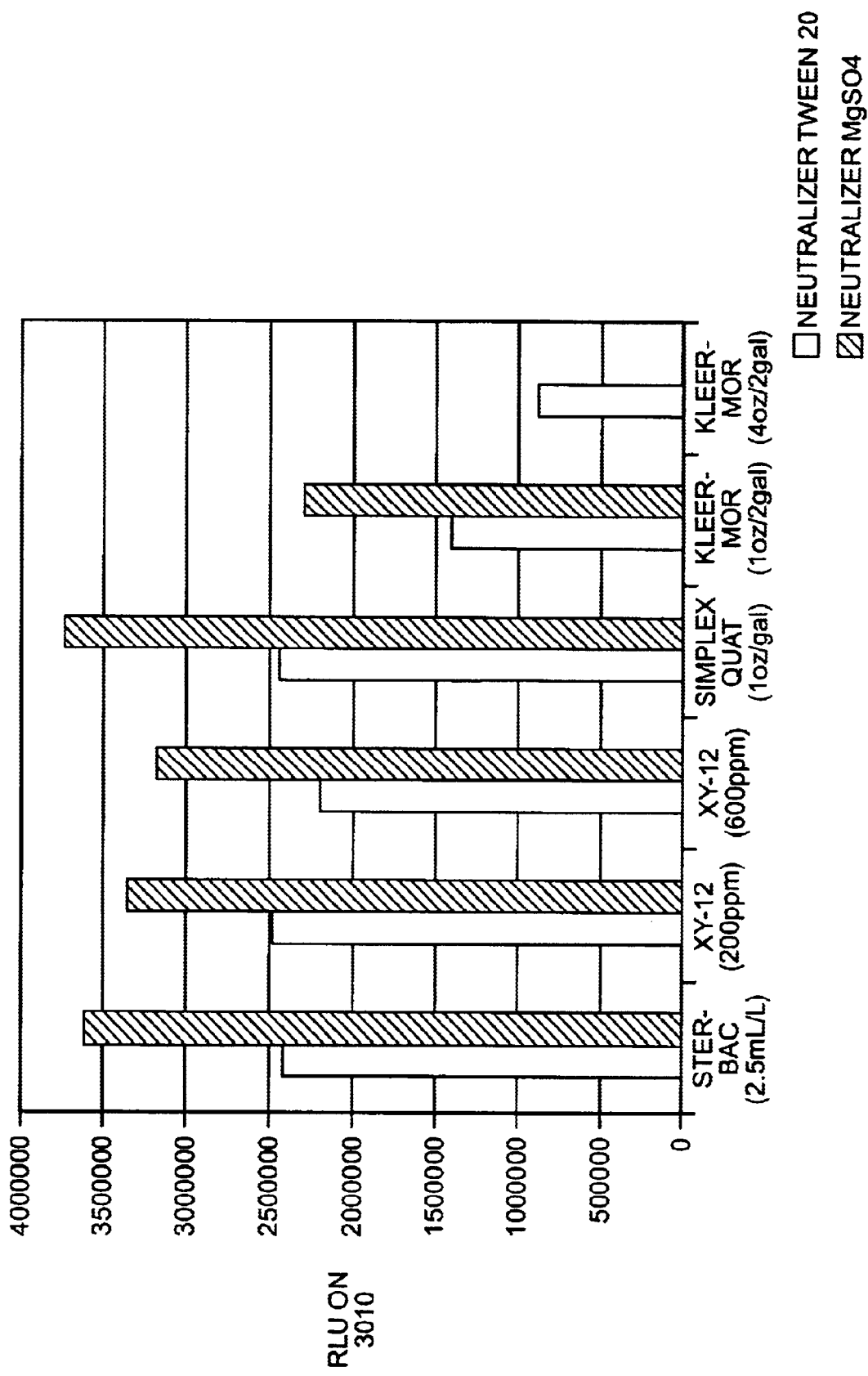
FIG. 2 shows a comparison of the effect of Tween® 20 and $MgSO_4$ on the intensity of light in the presence of various sanitizers, ATP-luciferin-luciferase solution and extractant.

FIG. 2 compares the effect of Tween® 20 and $MgSO_4$ on the intensity of light in the absence of extractant and in the presence of various sterilizers (1) Ster-Bac® (2.5 ml/L), (2) XY-12 (200 ppm), (3) XY-12 (600 ppm), (4) Simplex Quat (1 oz/gal), (5) Kleer-Mor® (1 oz/2 gal) and (6) Kleer-Mor® (4 oz/2 gal); and in the presence of (7) a Control.

Figure 3:
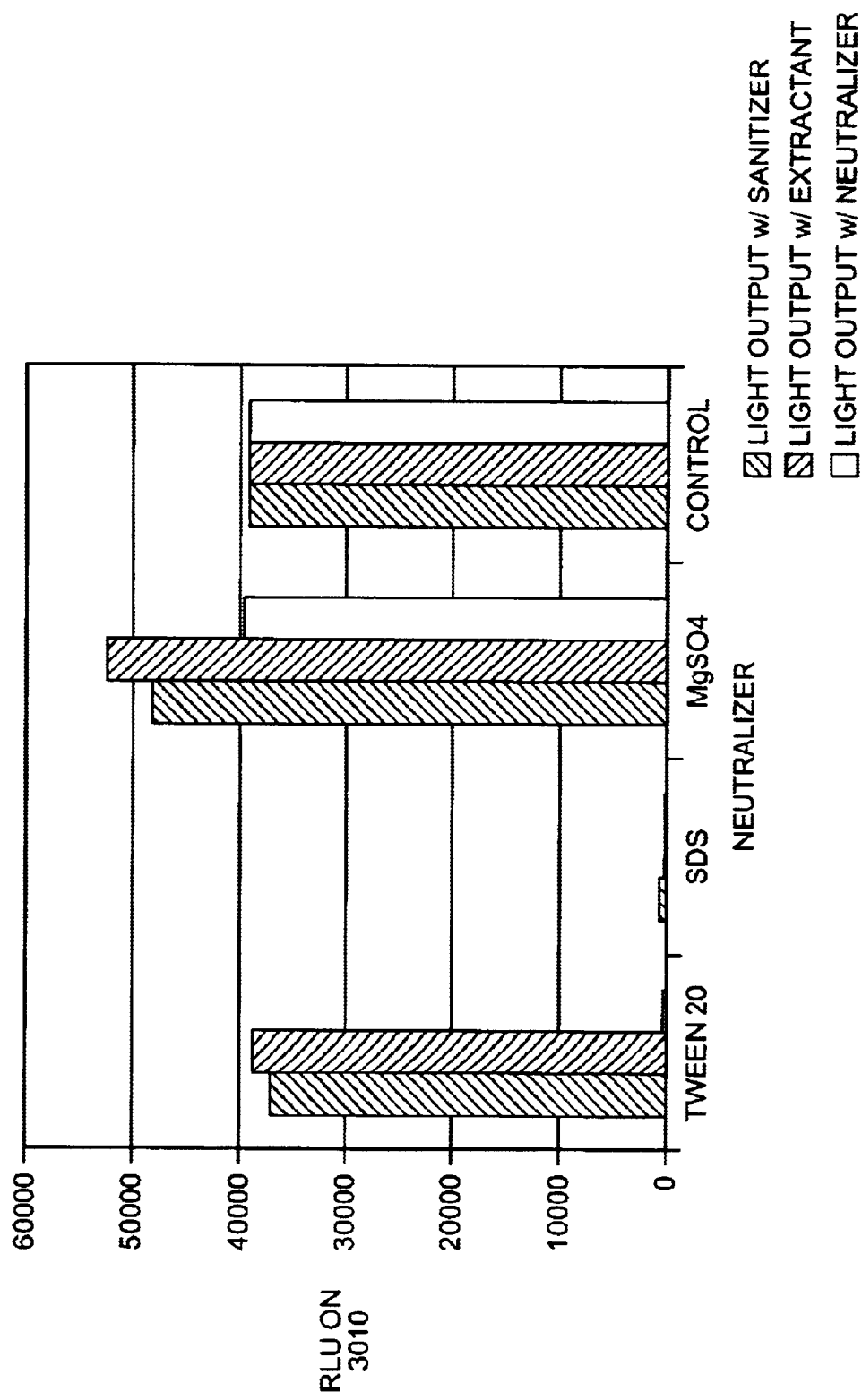
FIG. 3 shows a comparison of the effect of Tween® 20, SDS and $MgSO_4$ on the intensity of light (1) with sanitizer, (2) with extractant and (3) alone.

FIG. 3 compares the effect of (1) Tween® 20, (2) SDS and (3) $MgSO_4$ on the intensity of light (1) with sanitizer, (2) with extractant and (3) alone.

Figure 4A:
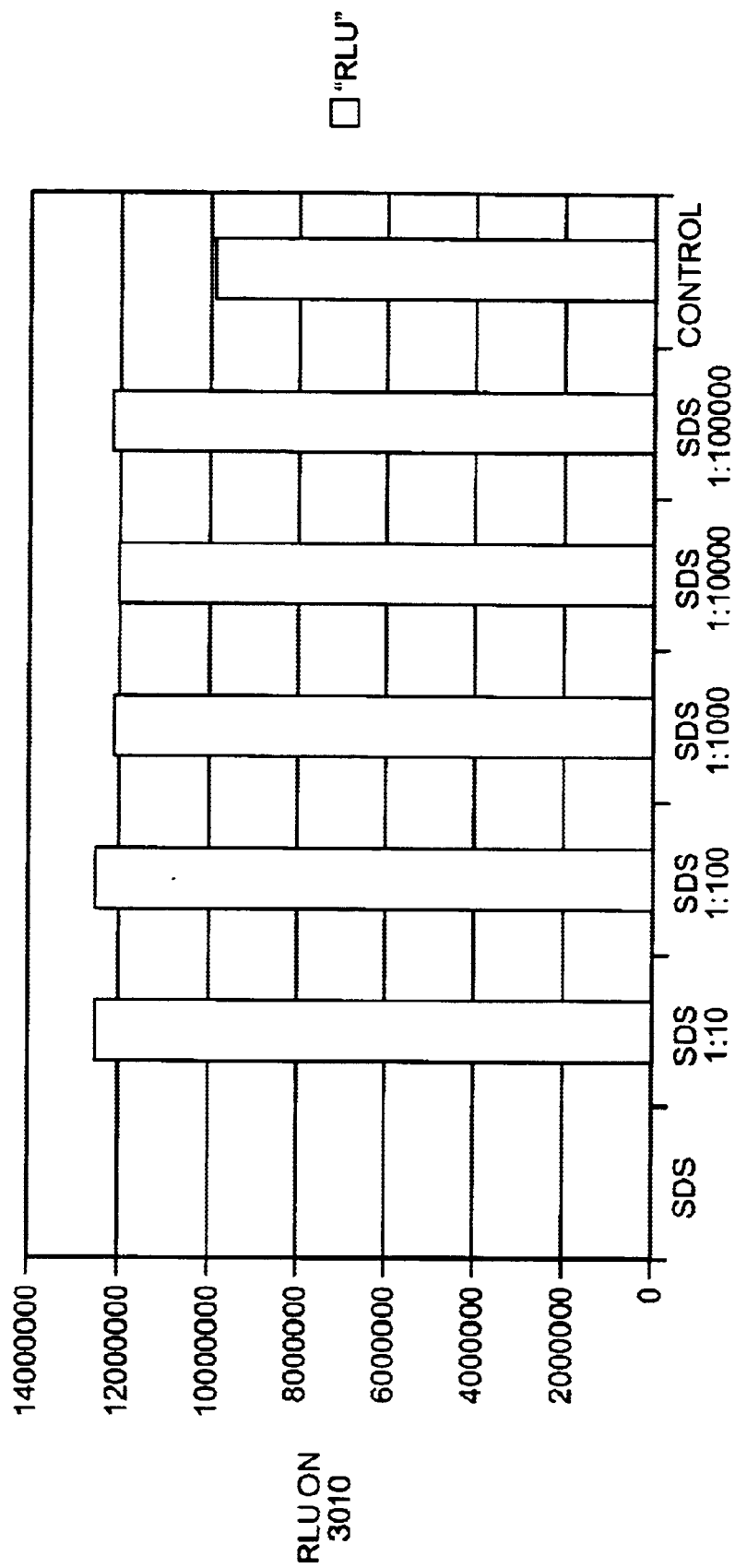
FIGS. 4A and 4B show a comparison of the effect of SDS at various concentrations on the intensity of light in the presence of sanitizer and ATP-luciferin-luciferase solution.
Figure 4B:
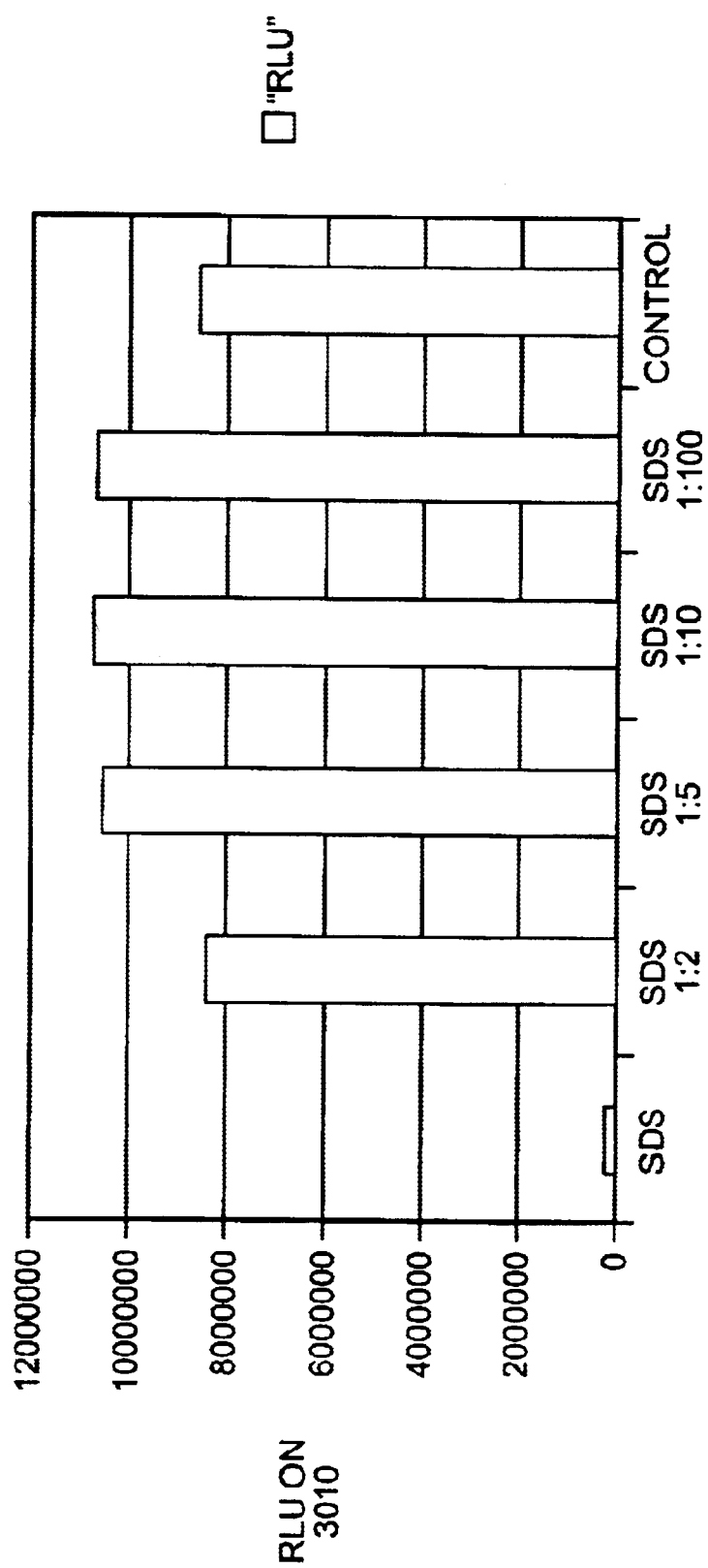

FIGS. 4A and 4B compare the effect of SDS at various concentrations, i.e., 0, 1:10, 1:100, 1:1000, 1:10000, 1:100000 (FIG. 4A) and 0, 1:2, 1:5, 1:10, 1:100 (FIG. 4B), on the intensity of light in the presence of sanitizer and ATP-luciferin-luciferase solution.

Figure 4C:
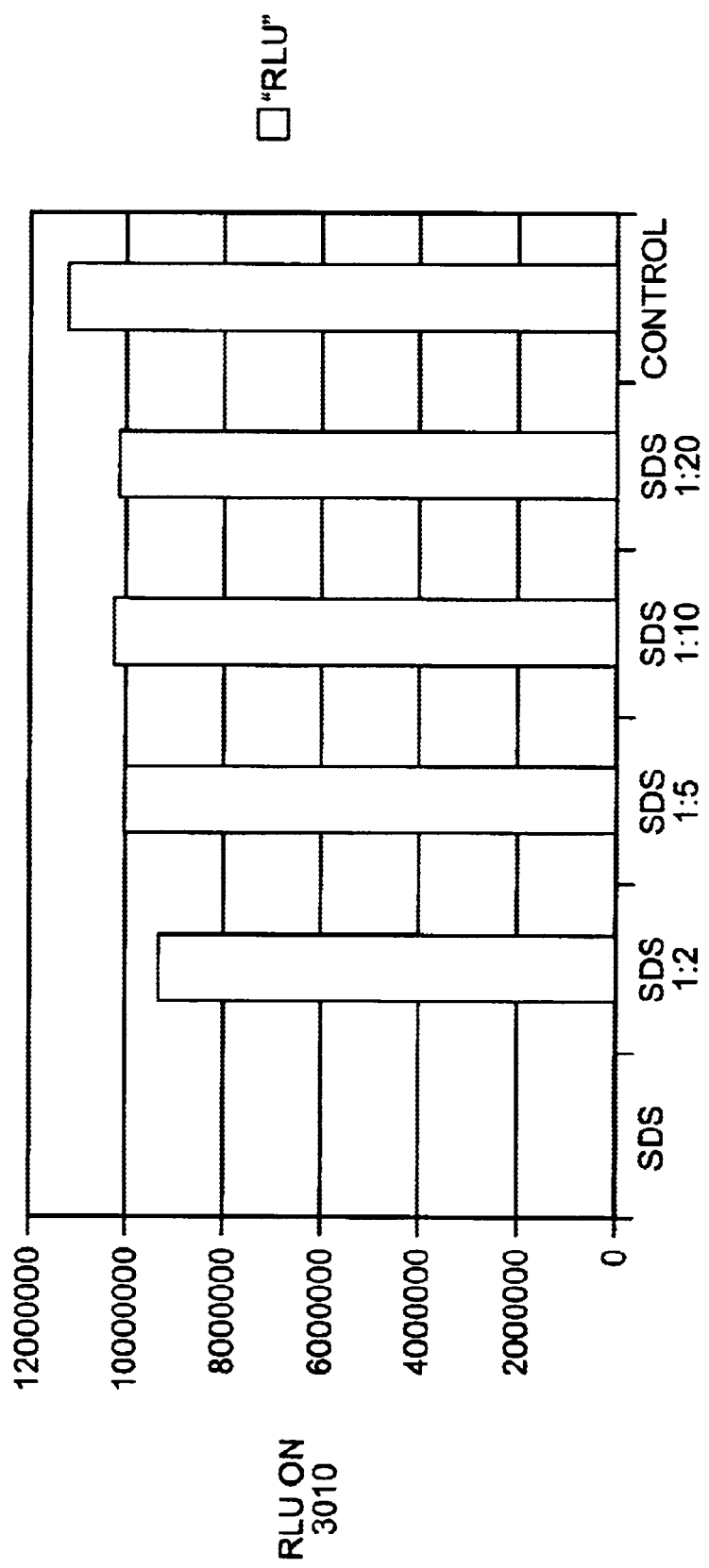
FIG. 4C shows a comparison of the effect of SDS at various concentrations on the intensity of light in the presence of extractant, sanitizer and ATP-luciferin-luciferase solution.

FIG. 4C compares the effect of SDS at various concentrations, i.e., 0, 1:2, 1:5, 1:10, 1:20, on the intensity of light in the presence of extractant, sanitizer and ATP-luciferin-luciferase solution.

Figure 5:
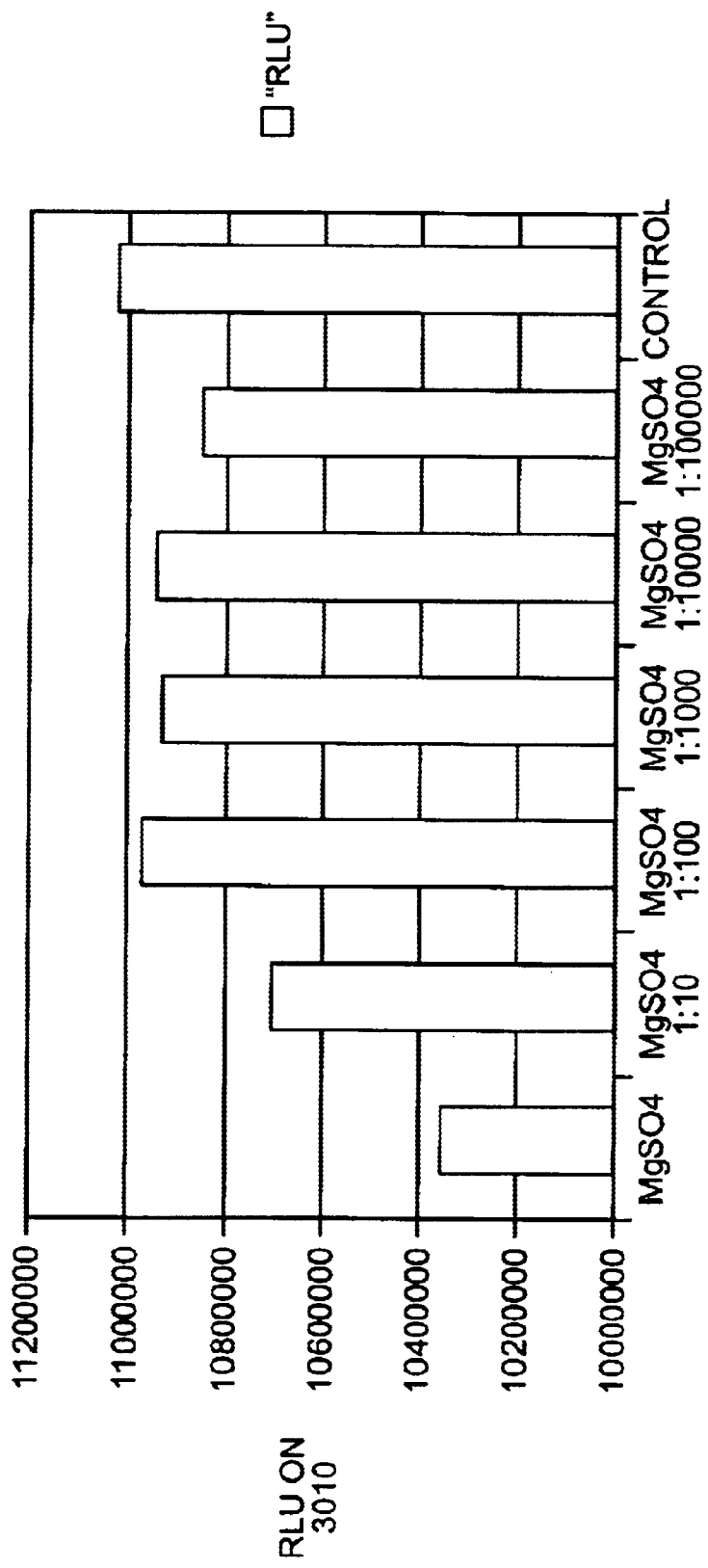
FIG. 5 shows a comparison of the effect of $MgSO_4$ at various concentrations on the intensity of light in the presence of extractant, sanitizer and ATP-luciferin-luciferase solution.

FIG. 5 compares the effect of $MgSO_4$ at various concentrations, i.e., 0, 1:10, 1:100, 1:1000, 1:10000, 1:100000, on the intensity of light in the presence of extractant, sanitizer and ATP-luciferin-luciferase solution.

Figure 6A:
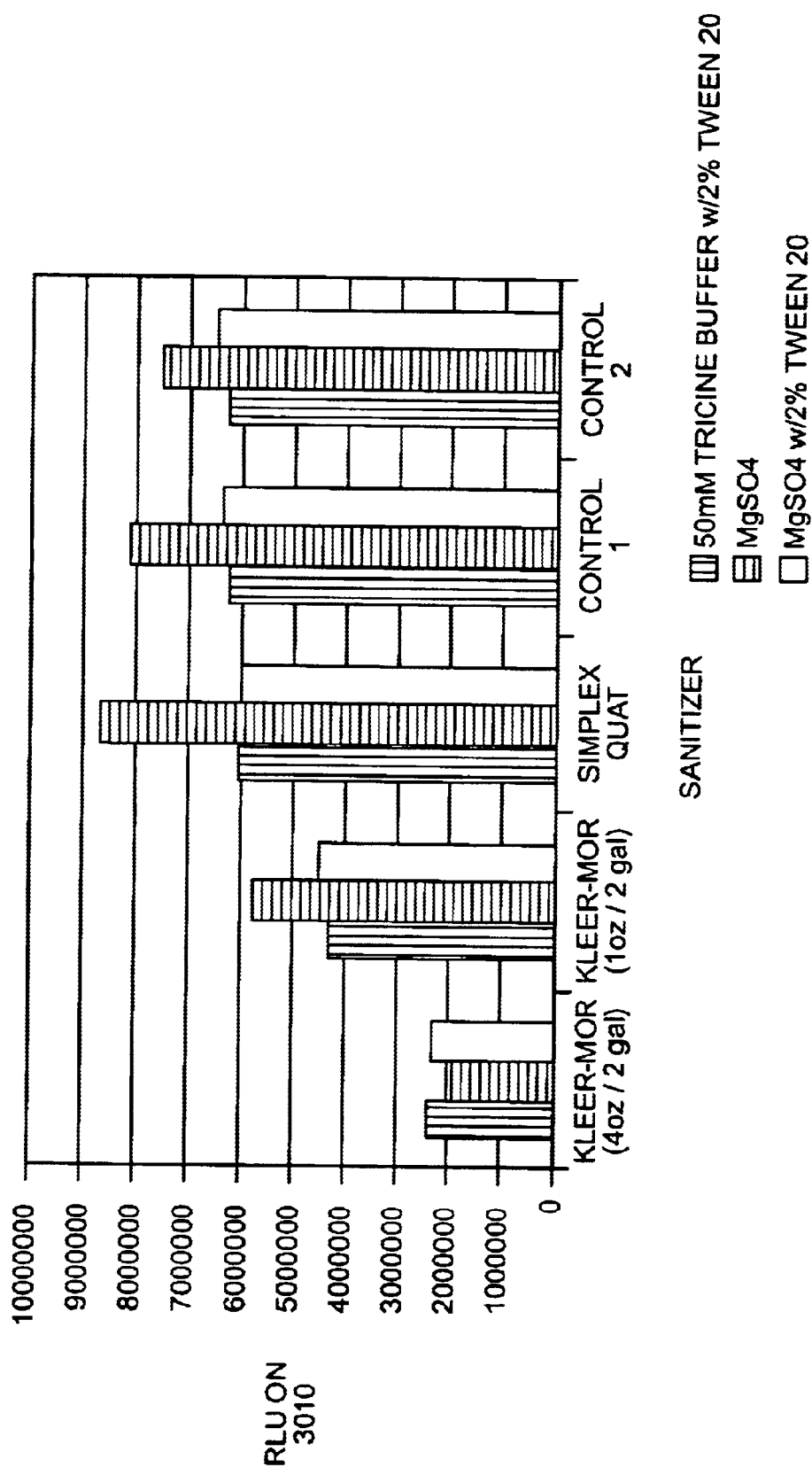
FIGS. 6A and 6B show a comparison of the effect of (1) Tween® 20 alone, (2) $MgSO_4$ alone and (3) $MgSO_4$ and Tween® 20 (at various concentrations) on the intensity of light in the presence of extractant, sanitizer and ATP-luciferin-luciferase solution.
Figure 6B:
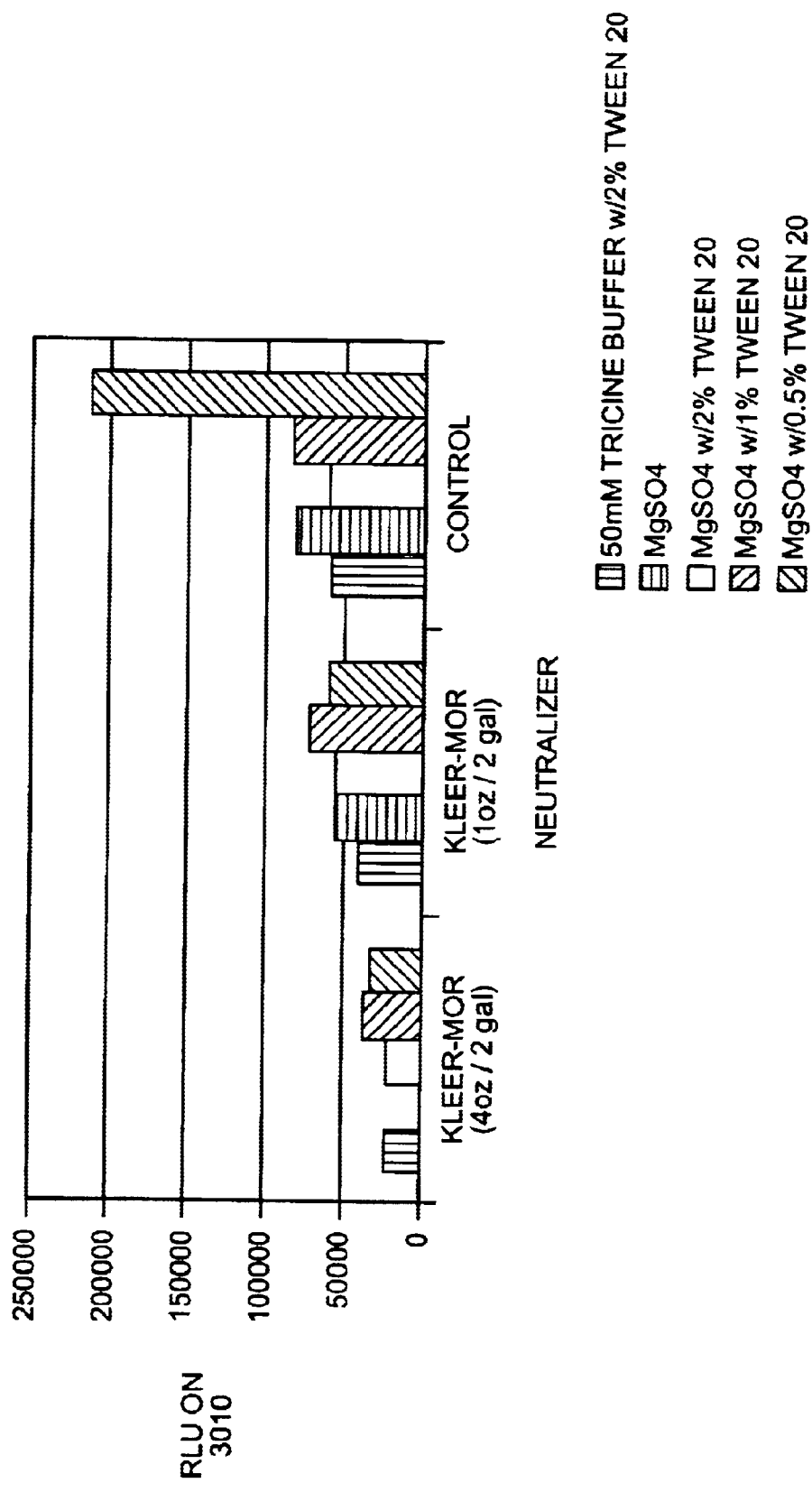

FIG. 6A compares the effect of various concentrations of (1) Tween® 20 alone, (2) $MgSO_4$ alone and (3) Tween® 20 and $MgSO_4$ on the intensity of light in the presence of extractant, sanitizer and ATP-luciferin-luciferase solution. FIG. 6B compares the effect of various concentrations of (1) Tween® 20 alone,
(2) $MgSO_4$ alone, (3) 2% Tween® 20 and $MgSO_4$, (4) 1% Tween® 20 and $MgSO_4$, and (5) 0.5% Tween® 20 and MgSO$_4$, on the intensity of light in the presence of extractant, sanitizer and ATP-luciferin-luciferase solution.

Figure 7:
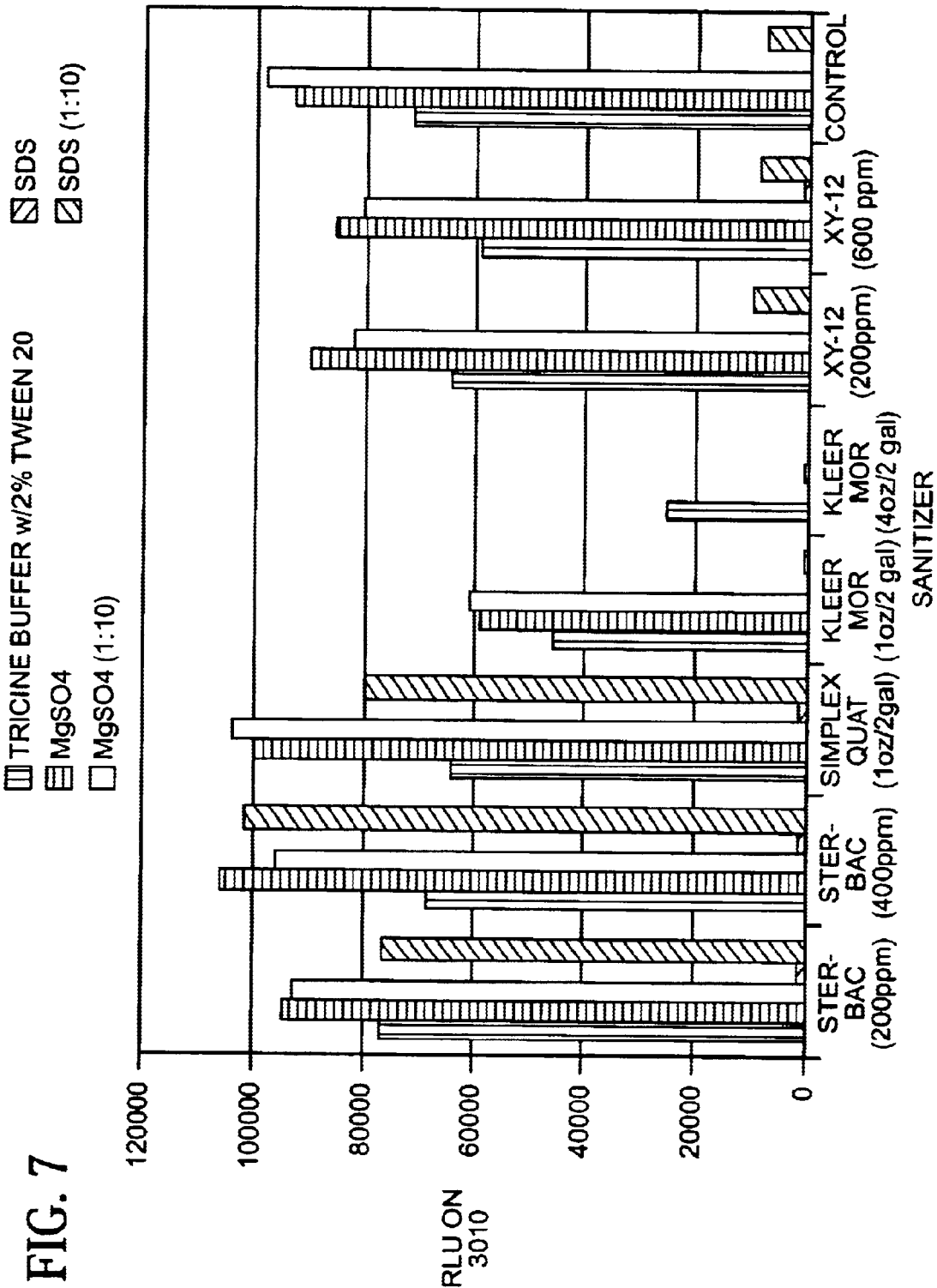
FIG. 7 shows a comparison of the effect of $MgSO_4$ and SDS at various concentrations on the intensity of light in the presence of extractant, sanitizer and ATP-luciferin-luciferase solution.

FIG. 7 compares the effect of various concentrations of (1) MgSO$_4$ and (2) SDS on the intensity of light in the presence of extractant, sanitizer and ATP-luciferin-luciferase solution.

Results

At equal concentrations of neutralizer (anionic substance) and positively charged extractant, the following was observed:

1. MgSO$_4$ performed better than Tween® 20 as a neutralizer for all sanitizers except one (Kleer-Mor® (4 oz/2 gal)). See FIGS. 1 and 2. MgSO$_4$ performed better than SDS in all assays. See FIG. 3.
2. The SDS solution was not effective and inhibited the light reaction. See FIG. 3.

At diluted concentrations of MgSO$_4$ and SDS as compared to the positively charged extractant, the following was observed:

1. The diluted MgSO$_4$ increased light intensity over the undiluted MgSO$_4$. See FIG. 5.
2. The SDS diluted 1:2 or more did not affect (inhibit) light intensity and was effective in neutralizing the inhibitory effects of benzalkonium chloride. See FIGS. 4A, 4B and 4C.

The neutralizing effect of MgSO$_4$ alone and in combination with Tween® 20 or sanitizers was determined. See FIG. 6A. The results demonstrate that MgSO$_4$ alone works at least as well and, in most cases, better than Tween® 20 in neutralizing the effects of sanitizer.

MgSO$_4$ with 1% Tween® 20 had the best performance with sodium triphosphate sanitizers (Kleer-Mor®). See FIG. 6B.

These results demonstrate that MgSO$_4$ at amounts between about 0.0001 µg and about 0.1052 µg and that SDS at amounts between® about 0.0001 µg and about 0.0246 µg were effective in neutralizing the inhibitory effect(s) that commonly employed extractants such as benzalkonium chloride have on the ATP-luciferin-luciferase light reaction.

These results also demonstrate that sulfate is more effective than Tween® 20 in neutralizing the inhibitory effect(s) that commonly employed extractants such as benzalkonium chloride have on the ATP-luciferin-luciferase light reaction. The results also show that SDS, at the proper concentrations, also neutralizes the inhibitory effect(s) that commonly employed extractants have on the ATP-luciferin-luciferase light reaction.

Having now fully described the invention, it will be apparent to one of ordinary skill in the art that changes and modifications can be made thereto without departing from the spirit or scope of the invention as set forth herein. Unless such changes and modifications depart from the scope of the invention, they should be construed as being included therein. It is intended, therefore, that the foregoing detailed description be understood from the following claims, including all equivalents, which are intended to define the scope of the invention.

What is claimed is:

1. A method for assaying for a presence of ATP in a sample, comprising:
    a) introducing a cationic extractant and an anionic substance, wherein said anionic substance is selected from the group consisting of sulfate ion and sodium dodecylsulfate (SDS);
    b) extracting said ATP from said sample;
    c) permitting luciferin and magnesium to react with said extracted ATP to form an ATP-magnesium-luciferin complex;
    d) allowing the ATP-magnesium-luciferin complex to interact with luciferase, wherein light is produced; and
    e) measuring an intensity of said light, wherein a presence of light corresponds to a presence of said ATP.

2. The method of claim 1, wherein said sulfate ion is in a form of a magnesium salt.

3. The method of claim 2, wherein said magnesium salt is magnesium sulfate.

4. The method of claim 3, wherein said magnesium sulfate is present in an amount of about 0.0001 µg to about 0.4 µg.

5. The method of claim 1, wherein said anionic substance is SDS in an amount of about 0.0001 µg to about 0.5 µg.

6. A method for detecting an amount of ATP extracted from a sample, comprising:
    a) introducing a cationic extractant and an anionic substance, wherein said anionic substance is selected from the group consisting of sulfate ion and sodium dodecylsufate (SDS);
    b) extracting said ATP;
    c) permitting luciferin and magnesium to react with said extracted ATP to form an ATP-magnesium-luciferin complex;
    d) allowing the ATP-magnesium-luciferin complex to interact with luciferase, wherein light is produced; and
    e) measuring an intensity of said light, wherein said intensity of said light corresponds to an amount of ATP extracted.

7. The method of claim 6, wherein said sulfate ion is in a form of a magnesium salt.

8. The method of claim 7, wherein said magnesium salt is magnesium sulfate.

9. The method of claim 8, wherein said magnesium sulfate is present in an amount of about 0.0001 µg to about 0.4 µg.

10. The method of claim 6, wherein said anionic substance is SDS in an amount of about 0.0001 µg to about 0.5 µg.

11. A method for detecting contamination in a sample, comprising:
    a) introducing a cationic extractant and an anionic substance, wherein said anionic substance is selected from the group consisting of sulfate ion and sodium dodecylsulfate (SDS);
    b) extracting said ATP;
    c) permitting luciferin and magnesium to react with said extracted ATP to form an ATP-magnesium-luciferin complex;
    d) allowing the ATP-magnesium-luciferin complex to interact with luciferase, wherein light is produced; and
    e) measuring an intensity of said light, wherein said intensity of said light corresponds to a presence of said ATP, and wherein said presence of said ATP corresponds to contamination.

12. The method of claim 11, wherein said sulfate ion is in a form of a magnesium salt.

13. The method of claim 12, wherein said magnesium salt is magnesium sulfate.

14. The method of claim 13, wherein said magnesium sulfate is present in an amount of about 0.0001 µg to about 0.4 µg.

15. The method of claim 11, wherein said anionic substance is SDS in an amount of about 0.0001 µg to about 0.5 µg.

* * * * *